(12) United States Patent
Gan et al.

(10) Patent No.: US 7,673,515 B2
(45) Date of Patent: Mar. 9, 2010

(54) VIBRATION SENSOR

(75) Inventors: Livne Gan, Midreshet Ben Gurion (IL); Sever-Yoan Mican, Tel-Hashomer (IL); Lior Nachom, Yavne (IL)

(73) Assignee: Spider Technologies Secutiry Ltd., Lod (IL)

(*) Notice: Subject to any disclaimer, the term of this patent is extended or adjusted under 35 U.S.C. 154(b) by 489 days.

(21) Appl. No.: 11/572,520

(22) PCT Filed: Jul. 26, 2005

(86) PCT No.: PCT/IL2005/000797

§ 371 (c)(1),
(2), (4) Date: Jan. 23, 2007

(87) PCT Pub. No.: WO2006/011145

PCT Pub. Date: Feb. 2, 2006

(65) Prior Publication Data

US 2009/0038397 A1   Feb. 12, 2009

Related U.S. Application Data

(60) Provisional application No. 60/590,896, filed on Jul. 26, 2004.

(51) Int. Cl.
*G01H 3/00* (2006.01)
*E21B 47/10* (2006.01)

(52) U.S. Cl. .................. 73/592; 73/152.18; 73/628; 73/649

(58) Field of Classification Search .................. 73/592, 73/649, 622, 624, 628, 152.47, 152.18
See application file for complete search history.

(56) References Cited

U.S. PATENT DOCUMENTS

| 3,204,457 A | 9/1965 | Howatt |
| 3,274,537 A | 9/1966 | Toulis |
| 3,455,150 A | 7/1969 | Wood |

(Continued)

FOREIGN PATENT DOCUMENTS

DE          3914895          11/1990

(Continued)

OTHER PUBLICATIONS

Written Opinion of the International Searching Authority published Jan. 26, 2007 for PCT/IL2005/00797 filed Jul. 26, 2005.

(Continued)

*Primary Examiner*—J M Saint Surin
(74) *Attorney, Agent, or Firm*—Martin Fleit; Paul D. Bianco; Fleit Gibbons Gutman Bongini & Bianco PL

(57) ABSTRACT

A method for measuring a vibration from four or more equidistant points in a chamber, comprising centering a chamber surface around a center point, containing a fluid within the chamber surface, measuring a fluid vibration from at least four measuring points in juxtaposition with the chamber surface, wherein at least two measuring points are located along a first axis passing through the center point and at least two measuring points are located along a second axis passing through the center point.

9 Claims, 3 Drawing Sheets

U.S. PATENT DOCUMENTS

| | | | |
|---|---|---|---|
| 4,083,255 A | | 4/1978 | McKechnie |
| 4,334,296 A | | 6/1982 | Hall, Jr. ................... 367/180 |
| 4,525,819 A | | 6/1985 | Hefer ...................... 367/188 |
| 4,536,696 A | | 8/1985 | Ray |
| 4,961,345 A | * | 10/1990 | Tsuruoka et al. ............ 73/32 A |
| 5,465,039 A | | 11/1995 | Narita et al. |
| 6,862,920 B2 | * | 3/2005 | Gysling et al. ............ 73/61.79 |
| 6,874,361 B1 | * | 4/2005 | Meltz et al. .............. 73/152.32 |
| 6,889,562 B2 | * | 5/2005 | Gysling et al. ........... 73/861.42 |
| 7,373,840 B2 | * | 5/2008 | Kamimura ............... 73/861.27 |
| 2003/0020610 A1 | | 1/2003 | Swanson et al. |
| 2004/0067005 A1 | | 4/2004 | Miyazawa et al. |
| 2005/0066736 A1 | | 3/2005 | Ohbayashi et al. |
| 2005/0083801 A1 | | 4/2005 | Kuo et al. |
| 2005/0115322 A1 | | 6/2005 | Lowrance |
| 2005/0137804 A1 | | 6/2005 | Permuy et al. |
| 2007/0038095 A1 | * | 2/2007 | Greenleaf et al. ........... 600/438 |

FOREIGN PATENT DOCUMENTS

| | | |
|---|---|---|
| EP | 0588569 A2 | 3/1994 |
| GB | 2358429 | 7/2001 |

OTHER PUBLICATIONS

International Preliminary Report on Patentability published Jan. 30, 2007 for PCT/IL2005/00797 filed Jul. 26, 2005.

International Search Report published Apr. 27, 2006 for PCT/IL2005/00797 filed Jul. 26, 2005.

* cited by examiner

VIBRATION SENSOR

FIELD OF THE INVENTION

The present invention relates to a vibration sensor having multiple transducers in contact with fluid contained within a sensor chamber.

BACKGROUND OF THE INVENTION

Determining the direction and/or intensity of vibrations provides valuable information in many diverse technological fields, for example, seismic plotting of an earthquake, locating tunnel activity, and intrusion event detection.

A common prior art vibration sensor comprises a transducer in contact with fluid in a chamber. As the fluid vibrates in response to vibrations that contact the chamber, the transducer produces a signal that is received by a signal interpreter. The interpreter uses the signal to characterize vibrations in magnitude, frequency or vector along an axis passing through the fluid.

To characterize a vibration in multiple axes, multiple sensors, each having a different axis, for example, are coupled together or alternatively, the sensor is rotated and/or moved with respect to the vibration; as seen in the following exemplary patents:

In U.S. Pat. No. 4,525,819, Hartley, John Edward teaches a geophone transducer that is partially submerged in a fluid and detects horizontal seismic waves.

In U.S. Pat. No. 4,334,296, Hall Jr., Ernest M. teaches a geophone comprising a fluid filled chamber having transducers in flexible top and bottom walls. Multiple geophones are used to provide output signals relating to the direction of the earth's motion.

SUMMARY OF THE INVENTION

An aspect of an embodiment of the present invention comprises a vibration sensor that simultaneously provides output signals along multiple axes of a vibration, the sensor having a vibration-transmitting housing surrounding a chamber, the chamber containing a fluid and having a surface substantially in contact with the fluid.

In an exemplary embodiment, the sensor further includes two or more paired vibration transducers positioned around the chamber, each transducer having a body including a first end; a second end; and a central axis segment between the first and second ends that passes through the center of the body, each body including a port adapted to communicate with a signal interpreter.

Each first transducer end is operatively associated with the housing. Each second transducer end includes a transducing element operatively associated with the chamber fluid.

In an exemplary embodiment, a first transducer pair and a second transducer pair are paired around the chamber so that a first axis passes through a first transducer of each pair, the center of the chamber and through a second transducer of each pair; the first and second transducer pairs providing vibration information from the center of the chamber.

In an exemplary embodiment, the axes passing through the first and second transducer pairs are planar and perpendicular to each other. Planar axes, as used herein, refer to axes that lie along a single flat plane.

In an exemplary embodiment, the sensor includes at least a third axis containing a transducer pair similarly paired in the manner of the first and second transducer pairs.

Optionally, at least three of the three axes passing through the transducer pairs are perpendicular to each other and thereby characterize vibrations in the X-, Y-, and Z-axes.

In an alternative exemplary embodiment, each transducer in at least one pair of transducers includes an amplification housing to amplify the vibrations.

A further aspect of the present invention comprises a method for measuring a vibration, using at least one first pair and at least one second pair of transducers.

As used herein, the word "fluid" designates "a continuous amorphous substance that tends to flow and to conform to the outline of its container" (Word Web© 2005) and includes any liquid or powder suspended in liquid comprising an inertial mass that is responsive to vibrations.

As used herein, "vibration" refers to the response of the chamber fluid to motion or oscillations outside the chamber originating in, inter alia, mechanical or geological systems; the chamber fluid vibration pressure being measurable in frequency and amplitude. ("Harris' Shock and Vibration Handbook", Fifth Edition; Edited by Cyril M. Harris and Allan G. Piersol)

As used herein, "transducer" refers to a device that converts the pressure of a shock or a vibratory motion into an optical, mechanical or electrical signal that is proportional to one or more motion parameters.

As used herein, "transducing element" refers to the portion of the transducer that converts the pressure of the vibration motion into a signal. (ibid)

There is thus provided a vibration sensor and method for measuring vibrations, the sensor having two or more paired transducers, the sensor comprising a chamber within a housing, the chamber including a center, a surface in which all portions of the surface are substantially equidistant from the chamber center and a volume of a vibration-sensitive fluid substantially in contact with the surface.

The sensor further includes two or more pairs of vibration-sensitive transducers, wherein each transducer of each of the two or more pairs is adapted to communicate with at least one signal interpreter. Each transducer has a body including a first end portion, a second end portion and a central axis segment passing axially through the center of the body, between the first end portion and the second end portion.

The first end portion is operatively associated with the chamber surface and includes a transducing element receptor portion, at least a portion of the transducing element portion being substantially in contact with the fluid. The second end portion is in operative association with the housing and each transducer pair of the two or more transducer pairs includes an axis passing through the central segment of a first transducer, the chamber center, and the central segment of a second transducer.

Optionally, the signal interpreter provides at least one of adding and subtracting the signals generated by each of the at least two pairs of transducers.

In an exemplary embodiment, the axes of the two or more transducer pairs are planar and at least one first axis passing through at least one first transducer pair is at least one of perpendicular and obliquely angled, with respect to at least one second axis passing through at least one second transducer pair.

Alternatively, the at least two transducer pairs comprise at least three transducer pairs, and the at least one third transducer pair that is at least one of:

Planar, and oblique with respect to the plane of the at least two planar transducer pairs and the at least one third transducer pair axis is perpendicular to the plane of the at least two transducer pairs.

Optionally, the at least three transducer pairs comprise at least four transducer pairs, and include at least one fourth transducer pair angled 45 degrees to the two or more planar axes.

Optionally, each transducer of at least one transducer pair includes an amplification housing.

An aspect of an embodiment of the present invention comprises a vibration sensor having one or more paired transducers, the sensor comprising a chamber within a housing, the chamber including a center, a surface in which all portions of the surface are substantially equidistant from the chamber center and a volume of a vibration-sensitive fluid substantially in contact with the surface.

In an exemplary embodiment, the present invention further includes one or more pairs of vibration-sensitive transducers, wherein each transducer is adapted to communicate with at least one signal interpreter, each transducer further having a body that includes a first end portion with a cross sectional area, a second end portion, and a central axis segment passing axially through the center of the body between the first end portion and the second end portion.

The first end portion, including a transducing element receptor portion and an amplification housing, comprises a support element projecting from the body and beyond the transducing element, the support including one or more walls that surround an amplification fluid and a membrane attached to the support element and enclosing the amplification fluid, the membrane further including an area in contact with the chamber fluid, the contact area being substantially greater than the first end portion cross section.

The second end portion is in operative association with the housing and each transducer pair of the one or more transducer pairs includes an axis passing through the central segment of a first transducer, the chamber center and the central segment of a second transducer.

An aspect of the present invention further includes a method for measuring a vibration from four or more equidistant points, comprising centering a chamber surface around a center point, filling the chamber with fluid, measuring a fluid vibration from at least four measuring points juxtaposed against the chamber surface, wherein at least two measuring points are located along a first axis passing through the center point and at least two measuring points are located along a second axis passing through the center point. Optionally, two or more of the at least four measuring points comprise transducers having amplification housings.

An aspect of the present invention includes a method for measuring a vibration from two or more equidistant points, comprising centering a chamber surface around a center point, containing a fluid within the surface, juxtaposing two or more vibration measuring elements in juxtaposition with the surface, placing an amplification housing over the two or more vibration measuring elements and measuring a fluid vibration from at least two measuring points juxtaposed against the chamber surface; wherein at least two measuring points are located along an axis passing through the center point.

BRIEF DESCRIPTION OF THE DRAWINGS

Exemplary non-limiting embodiments of the invention are described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale.

The attached figures are.

DESCRIPTION OF EXEMPLARY EMBODIMENTS

Vibration Sensor Operation

Figure 1:
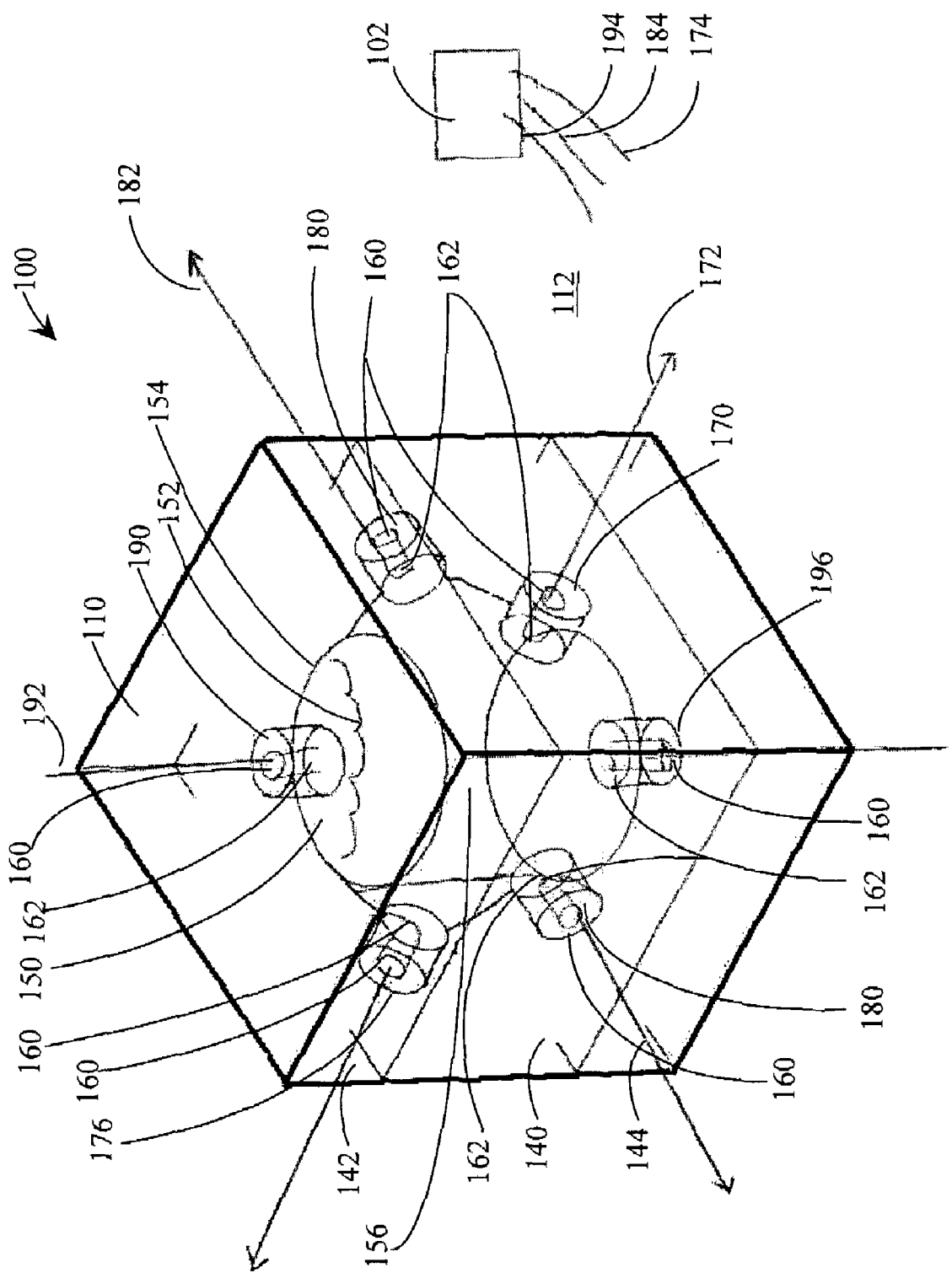
FIG. 1 shows a schematic view of a vibration sensor system, in accordance with an embodiment of the present invention.

FIG. 1 shows a schematic view of an exemplary embodiment of a vibration sensor 100 having a central, substantially spherical chamber 150, including a spherical surface 154 and a center 156. Chamber 150 contains a volume of fluid 152 and is surrounded by a housing 100 comprising a material adapted to transmit vibrations from an outside volume 112 to fluid 152, comprising, for example, a material including metal and/or plastic.

In an exemplary embodiment, chamber 150 includes six bores arranged into three pairs aligned with each of three axes 172, 182, and 192. A first bore 170 and a second bore 176 each have a central axis segment substantially aligned with an X-axis 172 that passes through center 156. A third bore 180 and a fourth bore 186 each have a central axis segment substantially aligned with a Y-axis 182 that passes through center 156. A fifth bore 190 and a sixth bore 196 each have a central axis segment substantially aligned with a Z-axis 192 that passes through center 156.

A vibration pressure transducer 160 is affixed, for example, with glue in each of bores 170, 176, 180, 186, 190 and 196, and includes a transducing element 162 substantially in contact with, and responsive to, the pressure of fluid 152 vibrations passing through chamber 150.

In an exemplary embodiment, a signal interpreter 102 is connected to each transducer 160 via paired cables 174, 184 and 194. X-axis paired cables 174 connect interpreter 102 to transducers 160 in bores 170 and 176. Y-axis cables 184 connect interpreter 102 to transducers 160 in bores 180 and 186. Z-axis cable 194 connect interpreter 102 to transducers 160 in bore 190 and 196.

Optionally, cables 174, 184 and 194, for example, comprise four electrical wires, two wires connecting to each transducer 160.

As used herein, the term "transducer 160" refers to any active or passive transducer 160, whose signal can be characterized by voltage, current amplitude, frequency, or phase. Active transducers 160 generate electrical signals from energy taken from the physical phenomenon being measured and include piezoelectric and inductive transducers 160. Passive transducers 160 measure the effect of the physical phenomenon on resistivity, capacity, or inductivity of an electric current and include resistive, capacitive, inductive, and opto-electronic transducers 160; some examples being Electret Condensers and coiled wire and magnet arrangements.

Alternatively, cables 174, 184 and 194 include wave guides and transducers 160 that transmit wave signals, for example, in infra red frequencies. In still other embodiments, each transducer provides a wireless signal that is received by receptor 102.

In an exemplary embodiment, signal interpreter 102 records information provided by the output of each transducer 160 individually and processes and/or analyzes the signal either during or following recording; using any one of the many signal analysis processes known in the art.

By way of example, interpreter 102 adds or subtracts signals from each set of two transducers 160 located on the X-172, Y-182 and/or Z-192 axes, thereby amplifying or attenuating signals and/or eliminating extraneous diffuse vibration noise; diffuse vibration noise referring to vibrations with the same amplitude and phase coming from all directions.

The resultant signal information from X-172, Y-182 and Z-192 axes is then processed by interpreter 102 to characterize a three-dimensional state of energy state of fluid 152 at center 156 along the X-172, Y-182 and/or Z-192 axes. This characterization, for example, provides frequency and magnitude information so that one sensor 100 can be used in place of multiple prior art sensors that each record along a single axis.

Figure 3:
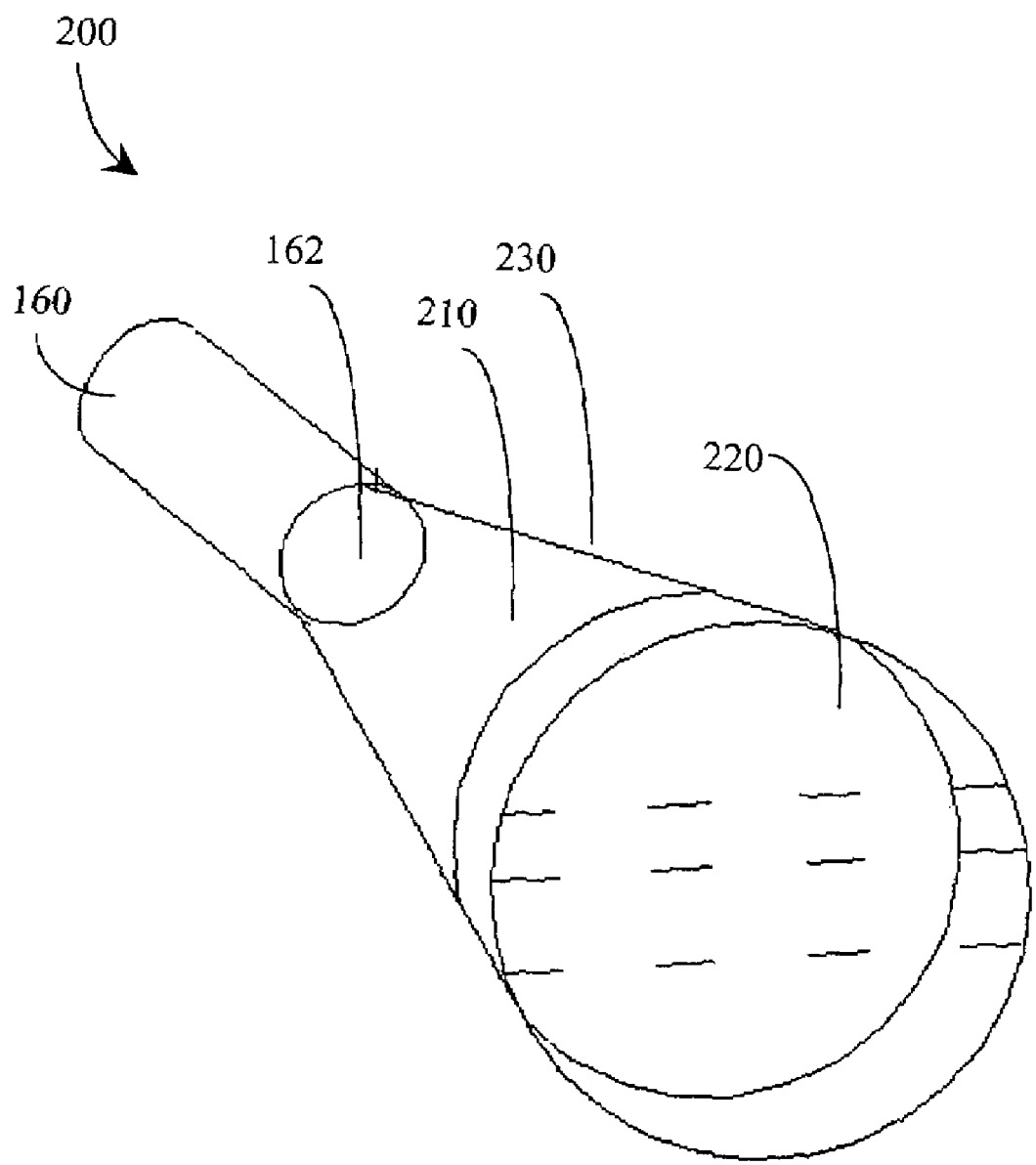
FIG. 3 shows a pressure transducer having an amplification diaphragm, in accordance with an embodiment of the present invention.

FIG. 3 shows an exemplary embodiment in which transducer 160 is modified to be responsive to weak signals. Modified transducer 160 includes an amplification housing 200 comprising a substantially rigid conical wall 230 having a vibration amplification membrane 220 that includes a large surface area. Wall 230, membrane 220, and a transducing element 262 enclose a volume of compressible amplification fluid 210, for example, a gas.

The pressure of each vibration against membrane 220 causes membrane 220 to deform wherein the pressure of fluid 210 is inversely proportional to volumetric changes according to the following formula:

$$P_1 = P_o \cdot \frac{V_o}{V_1}; \text{ wherein}$$

$P_o$=the pressure variation applied on membrane 220;
$P_1$=the pressure variation measured by transducing element 262;
$V_o$=the volume of fluid 210 before pressure Po is applied; and
$V_1$=the volume of fluid 210 after pressure variation Po is applied.

Based upon the above formula, vibration pressure on membrane 220 results in an elevated vibration pressure on transducing element 262; the resultant signal, for example, aiding interpreter 102 in distinguishing weak signals from background noise.

Vibration Sensor Variations

Vibration sensor 100 is not limited to the embodiments presented, but may be modified in many diverse ways, for example, providing unique configurations of sensor 100 for the many applications that are known to those familiar with the art. By way of example, only a few modifications of sensor 100 will now be presented.

In an exemplary embodiment, housing 110 comprises an upper section 142, a lower section 144 and a middle section 140. Alternatively, housing 110 is manufactured in one piece, for example using injection molding techniques.

As shown, X bores 170 and 176 and Y bores 180 and 186, are located in middle section 140 while Z bore 190 is located in upper section and Z bore 196 is located in lower section 144.

Additional pairs of bores (not shown) provide additional signal information to signal interpreter 102

Additionally or alternatively, three or more axes 172, 182 and 192 may pass through bores 170, 176, 180, 186, 190 and 106 at different angles for specific uses. To detect vibrations emitted from a distance, for example in detecting buried pipes supplying water, sensor 100 is optimally configured with multiple axes passing from upper section 142 to lower section 144 each at angles of between 0 and 90 degrees.

Alternatively, sensor 100 may include two pairs of transducers 160 along X-axis 172 and Y-axis 182 axes, accruing greater sensitivity to the signal information provided to signal interpreter 102.

Bores 170, 176, 180, 186, 190, and 196 along with their respective transducers 160 communicate with outside volume 112, and, together with the glue mentioned above, seal chamber 150. Alternatively, transducers 160 are mounted upon the inner surface of chamber 150 or embedded in housing 110 so that transducing elements 162 are recessed into surface 154.

Figure 2:
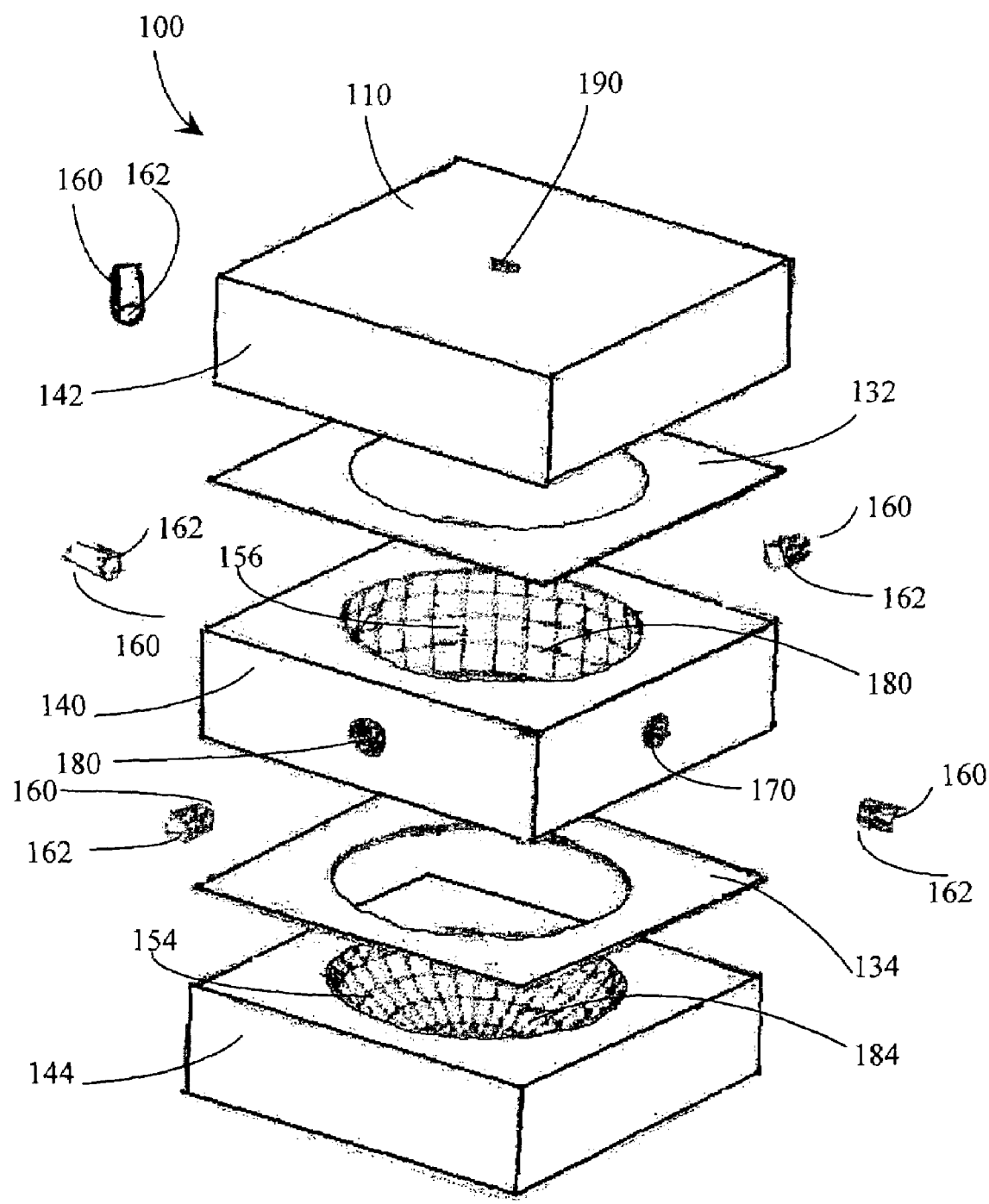
FIG. 2 shows a detailed exploded view of the vibration sensor of FIG. 1, in accordance with an embodiment of the present invention.

Proceeding to FIG. 2, sensor 100 is shown in an exploded view and includes an upper compressible gasket 132 between upper 142 and middle 140 sections; and a lower compressible gasket 134 between middle 140 and lowers 144 sections.

Gaskets 152 and 154, for example, comprise a compressible and/or flexible rubber material so that when bolts (not shown) extend vertically through the corners of sections 140, 142 and 144, gaskets 152 and 154 are compressed to seal chamber fluid 152 from outside volume 112.

Additionally or alternatively, gaskets 152 and 154 include upper and lower surfaces that adhere to adjacent surfaces of sections 140, 142 and 144, thereby aiding in sealing chamber 150.

Transducers 160 are shown having a cylindrical cross-section. Alternatively, transducers 160 have a rectangular cross-section, an elliptical cross-section, or other cross sectional shapes depending, for example, on the type of transducer 160 and/or application.

Additionally, the composition of fluid 152 varies depending upon the inertial mass characteristics required for a given application. For example, a high density fluid 152 such as liquid mercury may be required in some applications. Other applications are best served by particles, for example, a powdered metal alone or, for example, suspended in fluid 152; the many options for fluid 152 having specific characteristics being well know to those familiar with the art In some embodiments, fluid 152 substantially fills chamber 150 while in other embodiments, chamber 150 is partially filled. For example, in some embodiments, fluid fills 90% of chamber 150 to allow fluid 152 to expand due to anticipated temperature fluctuation.

In some embodiments, chamber 150 has a surface 154 that is substantially spherical while in other embodiments, surface 154 comprises several flat, intersecting planes, for example comprising a tetrahedron.

The many uses and embodiments of sensor 100, whether detection of seismic reflections, energy reaching a space station, or locating tunnel activity, are well known to those familiar with the art.

EPILOGUE

While the invention has been described with respect to a limited number of embodiments, it will be appreciated that many variations, modifications and other applications of the invention may be made.

Also, combinations of elements and/or variations in elements may be combined and single elements may be used, such variations and modifications, as well as others that may become apparent to those skilled in the art, are intended to be included within the scope of the invention, as defined by the appended claims.

The terms "include", "comprise" and "have" and their conjugates as used herein mean "including but not necessarily limited to."

It will be appreciated by a person skilled in the art that the present invention is not limited by what has thus far been described. Rather, the scope of the present invention is limited only by the following claims.

The invention claimed is:

1. A vibration sensor having two or more paired transducers, the sensor comprising:
   a chamber within a housing, the chamber including:
   a center;
   a surface in which all portions of the surface are substantially equidistant from the chamber center;
   a volume of a vibration-sensitive fluid substantially in contact with the surface; two or more paired vibration-sensitive transducers, wherein each transducer of each of the two or more pairs is adapted to communicate with at least one signal interpreter, each transducer further having a body including:
   a first end portion, a second end portion and a central axis segment passing axially through the center of the body, between the first end portion and the second end portion;
   the first end portion being operatively associated with the chamber surface and including a transducing element receptor portion, at least a portion of the transducing element portion being substantially in contact with the fluid;
   the second end portion being in operative association with the chamber housing;
   each transducer pair of the two or more paired transducers includes;
   an axis passing through the central segment of a first transducer;
   the chamber center; and
   the central segment of a second transducer.

2. A vibration sensor according to claim 1, wherein the signal interpreter provides at least one of:
   adding; and
   subtracting,
   the signals generated by each of the two or more paired transducers.

3. A vibration sensor according to claim 2, wherein the axes of the two or more paired transducers are planar.

4. A vibration sensor according to claim 3, wherein at least one first axis passing through at least one of the two or more paired transducers is at least one of:
   perpendicular; and
   obliquely angled,
   with respect to at least one second axis passing through at least one second transducer pair.

5. A vibration sensor according to claim 4, wherein the two or more paired transducers include at least one third transducer pair that is at least one of:
   perpendicular;
   oblique; and
   planar,
   with respect to the plane of the at least two planar transducer pairs.

6. A vibration sensor according to claim 5, including at least one fourth transducer pair angled 45 degrees to at least one of the transducer pairs.

7. A vibration sensor according to claim 2, wherein each transducer of au least one of the two or more paired transducers includes a first end portion having a cross sectional area, the first end portion further including an amplification housing, comprising:
   a transducing element receptor portion, a support element projecting from the body and beyond the transducing element;
   the support including one or more walls that surround an amplification fluid; and
   a membrane attached to the support element and enclosing the amplification fluid, the membrane further including an area in contact with the chamber fluid, the contact area being substantially greater than the first end portion cross section.

8. A vibration sensor having one or more one or more transducer pairs, the sensor comprising:
   a chamber within a housing, the chamber including:
   a center;
   a surface in which all portions of the surface are substantially equidistant from the chamber center;
   a volume of a vibration-sensitive fluid substantially in contact with the surface;
   one or more pairs of vibration-sensitive transducers, wherein each transducer is adapted to communicate with at least one signal interpreter, each transducer further including a body having:
   a first end portion having a cross sectional area;
   a second end portion in operative association with the chamber housing; and
   a central axis segment passing axially through the center of the body between the first end portion and the second end portion;
   the first end portion further including an amplification housing, comprising a transducing element receptor portion, a support element projecting from the body and beyond the transducing element, the support including one or more walls that surround an amplification fluid and a membrane attached to the support element and enclosing the amplification fluid, the membrane further including an area in contact with the chamber fluid, the contact area being substantially greater than the first end portion cross section;
   each transducer of the one or more transducer pairs including;
   an axis passing through the central segment of a first transducer;
   the chamber center; and
   the central segment of a second transducer.

9. A vibration sensor according to claim 8, wherein the signal interpreter provides at least one of:
   adding; and
   subtracting,
   the signals generated by each of the one or more one or more transducer pairs.

* * * * *